(12) United States Patent
Cesmeli

(10) Patent No.: US 6,434,215 B1
(45) Date of Patent: Aug. 13, 2002

(54) EKG-LESS CARDIAC IMAGE RECONSTRUCTION

(75) Inventor: Erdogan Cesmeli, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,943

(22) Filed: Jun. 28, 2001

(51) Int. Cl.$^7$ ................................. A61B 6/00
(52) U.S. Cl. ................... 378/8; 378/4; 378/20
(58) Field of Search ................... 378/4, 19, 20

(56) References Cited

U.S. PATENT DOCUMENTS

| | | | |
|---|---|---|---|
| 5,381,333 A | * 1/1995 | Isaacson et al. | 128/922 |
| 5,600,574 A | * 2/1997 | Reitan | 702/185 |
| 5,692,507 A | * 12/1997 | Seppi et al. | 128/920 |
| 6,236,705 B1 | * 5/2001 | Stergiopoulos et al. | 378/8 |

OTHER PUBLICATIONS

Cuiwei Li, Chongxun Zheng, and Changfeng Tai; "Detection of ECG Characteristic Points Using Wavelet Transforms"; IEEE Transactions on Biomedical Engineering, vol. 42, No. 1, Jan. 1995.

Stephane Mallat and Sifen Zhong; "Characterization of Signals from Multiscale Edges", IEEE Transactions on Pattern Analysis and Machine Intelligence, vol. 14, No. 7, Jul. 1992.

"Algorithms for Reconstruction with Nondiffracting Sources," Computerized Tomographic Imagaing, pp. 99–107.

* cited by examiner

*Primary Examiner*—David V. Bruce
*Assistant Examiner*—Pamela R. Hobden
(74) *Attorney, Agent, or Firm*—Armstrong Teasdale LLP

(57) ABSTRACT

A method for reconstructing an image of a beating heart in vivo is described. The method includes acquiring projection data for at least one z-location within a projection space, determining peaks in first order spatial moments for the projection space using the projection data, and reconstructing the image utilizing peaks in the first order spatial moments.

30 Claims, 2 Drawing Sheets

EKG-LESS CARDIAC IMAGE RECONSTRUCTION

BACKGROUND OF INVENTION

This invention relates generally to computed tomography (CT) imaging, and more particularly to reliable cardiac imaging using a CT system.

Generating an image of a human heart for diagnosis requires temporal and spatial resolution difficult to achieve. Specifically, during a CT scan, an x-ray source and an x-ray detector rotate around a patient as the patient heart continues to beat and cycle through various cardiac phases. The movement of the heart during the scan can result in undesirable image artifacts, and less than satisfactory temporal and spatial resolution.

If an entire three-dimensional (3D) volume of the heart could be scanned instantaneously during a particular cardiac phase, a cardiac image could be generated using image reconstruction methods which are the same as the reconstruction methods used for a non-moving body part. However, such a CT scan of a beating heart cannot be performed instantaneously.

Therefore, in cardiac imaging, positional data as well as cardiac data typically is obtained simultaneously with the scan, and such additional data is utilized in performing image reconstruction. Associating positional and/or cardiac data with the scan data sometimes is referred to herein as tagging. Such tagging is performed by storing the positional or cardiac data with the scan data itself (e.g., as a digital word) or by storing positional or cardiac data in a table that is correlated to the scan data.

With respect to the positional information, the z-location of the patient, or patient table, is associated with the acquired scan data so that the patient position for the particular scan data is known. Additionally, electrocardiogram (EKG) data is collected simultaneously with the scan data, and the scan data is tagged with the EKG data. The EKG data identifies the cardiac phase of the heart when the scan data was collected. As a result, and for the collected scan data, the z-location and cardiac phase are known. Collecting EKG data, however, requires EKG equipment and additional patient preparation.

By knowing the z-location at which scan data was collected, and by knowing the particular cardiac phase of the heart when such scan data was collected, then the scan data for a particular z-location during a particular cardiac phase can be identified and used in image reconstruction processing. For example, scan data for a particular z-location and a particular cardiac phase can be used to generate images having a desired spatial and temporal resolution. If scan data for different cardiac phases or different z-locations is utilized in generating such images, then such images may not have the desired spatial and temporal resolution.

SUMMARY OF INVENTION

In one aspect, a method is provided for reconstructing an image of a beating heart in vivo. The method includes acquiring projection data for at least one z-location within a projection space and for at least one cardiac cycle, determining peaks in first order normalized spatial moments for the projection space using the projection data, and reconstructing the image utilizing peaks in the first order spatial moments.

In another aspect, a system is provided for reconstructing an image of a beating heart in vivo. The system includes a computed tomography (CT) device including an x-ray source, an x-ray detector aligned with the x-ray source, a data acquisition system (DAS) for collecting data from the x-ray detector, and an image reconstructor for reconstructing an image from the collected data. The system acquires projection data for at least one z-location within a projection space and for at least one cardiac cycle, and correlates a plurality of views with z-location information, such that each view includes projection data acquired at the respective z-location. Furthermore, the system extracts projection data for a region of interest (ROI) within each z-location, determines peaks in first order spatial moments for the projection space using the projection data, and reconstructs the three-dimensional image utilizing peaks in the first order spatial moments.

In yet another aspect, a computer readable medium encoded with a program is provided for processing projection data for at least one z-location within a projection space, and for at least one cardiac cycle, to construct images of a beating heart in vivo. A computer, operating under the control of the program, extracts projection data for a region of interest (ROI) within each z-location, and determines peaks in first order spatial moments for the projection space using the projection data.

DETAILED DESCRIPTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) a viewable image.

Figure 1:
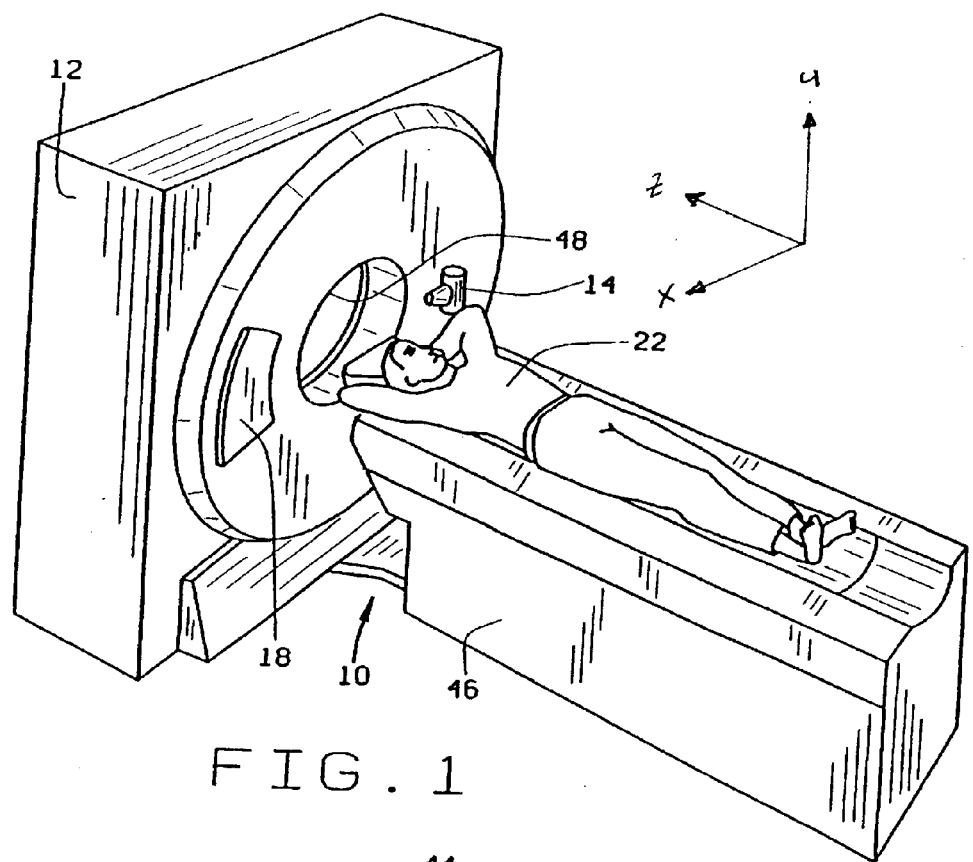
FIG. 1 is a pictorial view of a CT imaging system.
Figure 2:
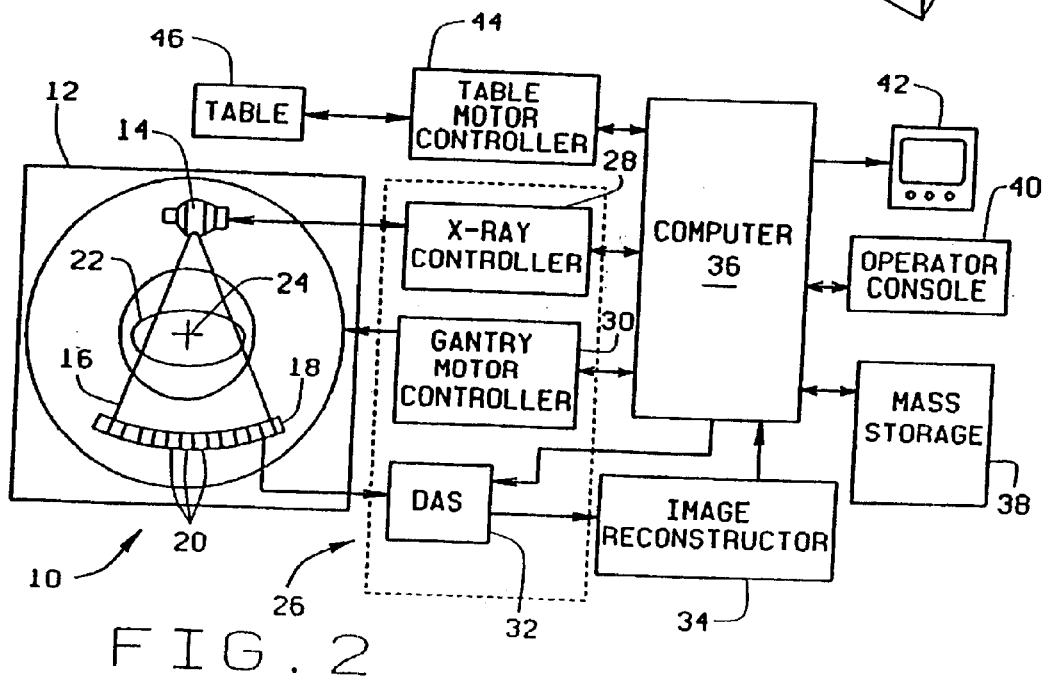
FIG. 2 is a block schematic diagram of the system illustrated in FIG. 1.

Referring to FIGS. 1 and 2, a computed tomograph (CT) imaging system 10 is shown as including a gantry 12 that is representative of a "third generation" CT scanner. Gantry 12 has an x-ray source 14 that projects a beam of x-rays 16 toward a detector array 18 on an opposite side of gantry 12. The fan-shaped x-ray beam is collimated to lie within an X-Y plane of a Cartesian coordinate system and is generally referred to as the imaging plane. Detector array 8 is formed by detector elements 20, which combine to sense the projected x-rays that pass through a medical patient 22. Each detector element 20 produces an electrical signal that represents the intensity of an impinging x-ray beam and hence, the attenuation of the beam as it passes through patient 22. The attenuation measurements, sometimes referred to as projection data, from all elements 20 are acquired separately to produce a transmission profile. During a scan to acquire x-ray projection data, gantry 12 and the components mounted thereon rotate about a center of rotation 24.

Detector array 18 includes a plurality of detector rows (not shown), which include a plurality of detector elements 20. Detector elements 20 in each detector row are positioned adjacent each other in the x-direction, and the detector rows are positioned adjacent each other in the z-direction. Thus, within detector array 18, for each detector element 20 in a detector row there are adjacent detector elements 20 in the z-direction equal to the number of detector rows, thereby forming columns in the z-direction. Each column includes a number of detector elements 20 equal to the number of detector rows, and detector array 18 includes a number of columns equal to the number of detector elements 20 in a detector row.

X-ray source 14 and detector array 18 rotate with gantry 12 within the imaging plane and around an object to be imaged so that the angle at which the x-ray beam intersects the object constantly changes. A group of x-ray attenuation measurements, i.e., projection data, from detector array 18 at one gantry angle is referred to as a view. A scan of the object comprises a set of views at different gantry angels, or view angles, during one revolution of x-ray source 14 and detector array 18.

At each gantry angle, detector array 18 generates a number of views equivalent to the product of the number of rows in detector array 18, for example 4, and the number of detector elements 20 in each row, for example N. For example, and at each gantry angle, 4N views are generated. To generate projection data for a specific z-location, data from various views are utilized in performing interpolation or extrapolation.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized data from DAS 32 and performs high speed image reconstruction. The reconstructed image is applied as an input to a computer 36, which stores the image in a mass storage device 38.

Computer 36 also receives commands and scanning parameters from an operator via a console 40 that includes a keyboard (not shown). An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. More specifically, table 46 moves portions of patient 22 through gantry opening 48.

In an axial scan, the projection data is processed to construct an image that corresponds to a two-dimensional slice taken through the object. In a "helical" scan, the patient is moved while the data for the prescribed number of slices is acquired, thereby generating a single helix from a fan beam. The helix mapped out by the fan beam yields projection data from which images in each prescribed slice may be reconstructed.

Cardiac reconstruction in multislice volume CT provides a 3D image of the heart at a given cardiac phase wherein the 3D volume is formed by a stack, or sequence, of parallel axial images. Helical scanning provides more axial coverage for a given breath-hold time, therefore, the image reconstruction method and system described below are based on a protocol employing helical projections. However, the method and system are not limited practice with helical scans, and other scan types, such as an axial scan, can be employed. Additionally, system 10 is described herein by way of example only, and the image reconstruction method and system described below can be practiced in connection with many other types of imaging systems, for example, an imaging system configured to collect cine scan data. Furthermore, the image reconstruction method, or algorithm, described herein is typically performed by image reconstructor 34. Such method, however, could be implemented in other components of the imaging system such as in computer 36.

Figure 3:
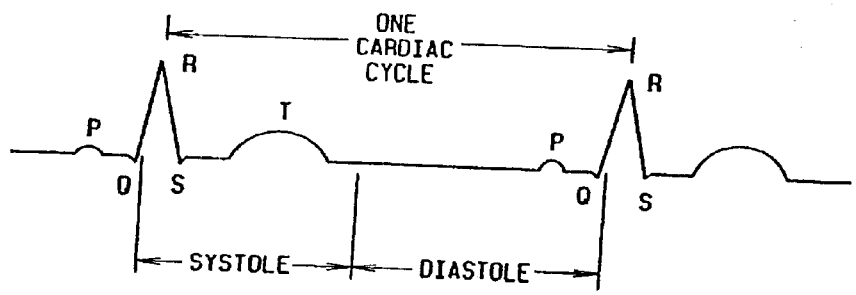
FIG. 3 is an EKG signal waveform used in known imaging systems.

FIG. 3, illustrates one cardiac cycle of an EKG signal waveform, including a systole condition, or period, and a diastole condition, or period, of the heart. The portions of the EKG signal labeled Q, R and S are referred to as the QRS complex, in which the R-feature, or R-wave, is the most prominent, highest amplitude, feature of the entire EKG signal. The cardiac cycle is typically defined as beginning with an R-wave and continuing until the occurrence of a next R-wave.

In one embodiment, during a cardiac CT scan, projection data is acquired from detector array 18 as table 46 moves a patient through gantry 12 at a fixed speed. A single projection data set is generated by each detector element 20 for a given position of gantry 12. As projection data is acquired while table 46 moves in the z-direction, each view is correlated, or 'tagged', with z-location information. In the example embodiment, computer 36 computes the z-location information and tags each view using information communicated from detector array 18, table motor controller 44, and gantry 12. For example, computer 36 utilizes a starting z-location of table 46, a period of gantry 12, and a table speed generated by motor controller 44 to compute a z-location for a corresponding view.

Figure 4:
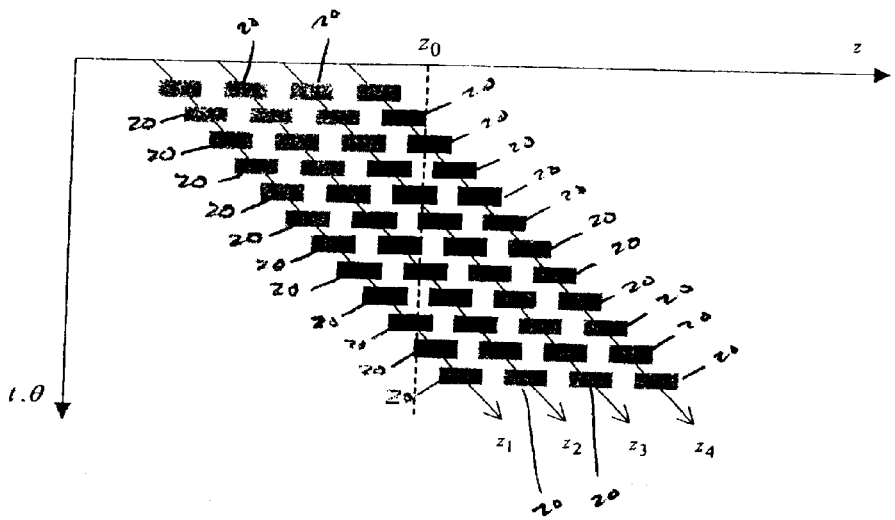
FIG. 4 is a representation of the spatial domain of a CT scan.

FIG. 4 is a representation of the spatial domain of projection data from a CT scan. Components in FIG. 4 identical to components in FIG. 2 are identified in FIG. 4 using the same reference numerals used in FIG. 2. Given the nature of a helical scan, not all views from detector elements 20 of any given column fall in the same z-plane. As such, CT projections can be visualized in a z-t domain, as shown in FIG. 4, wherein a horizontal group of four rectangles represent the z-location of four rows of detector elements 20, or those of their projections, across time. During a CT scan, projections in each detector row have linearly increasing z-heights, resulting in slanted trajectories.

In contrast, if the projections were from a cine scan mode, the rectangles would be aligned vertically, or in the same z-plane. For helical reconstruction, a vertical line in the z-t domain is formed by interpolation.

Interpolation in the z-direction takes place across multiple detector rows having detector elements 20 lying in the z-plane. For example, at a particular location, such as $z_0$, different detector rows, i.e. $z_1$, $z_2$, $z_3$, and $z_4$, have at least one detector element 20, shown in FIG. 4 as rectangles, lying in the z-plane. The different detector rows provide the z-coverage at different time intervals. The dark rectangles in FIG. 4 indicate detector elements 20 that contribute to interpolation.

Due to the geometry of detector array 18, detector elements 20 pass through $z_0$ as table 46 moves forward thereby providing a plurality of projection data, or views, with z-locations at $z_0$ at a given time t. As shown in FIG. 4, each detector row includes at least one detector element 20 lying in the z-plane and is therefore used for interpolation. The projection data from each detector element 20 lying in a desired z-plane, for example the $z_0$-plane, is used to interpolate a set of projection data at the desired z-location.

Different regions in a space domain correspond to different projections in the projection space. After the views are tagged with z-location data and combined using interpolation, the beginning and the end projections for each view of a specific region of interest (ROI) are extracted. In an exemplary embodiment, motion analysis is performed to determine a ROI, which encompasses a specific region of the projection space, such as the heart region. The ROI data is automatically extracted, i.e. without user input, from the projection data at a plurality of z-locations, for example $z_0$. During each rotation of the gantry, 984 views are acquired. For each of the 984 views, an average view is obtained by averaging the same view from multiple rotations. As a result, a set of average views is obtained that includes projection data for each of the 984 average views. During the automatic extraction process, the average set of views is subtracted from the view set of each individual rotation of gantry 12. The resulting view sets for each rotation have two major regions. More specifically, the resulting view sets have projection data that deviate from the projection data in the average view both maximally and minimally. The projection data that differs from the average projection data maximally are assumed to correspond to the region of interest.

In one embodiment, automatic extraction is accomplished using an algorithm executed by computer 36 and stored in any computer readable medium capable of storing electronic data. However, the automatic extraction could be performed utilizing image reconstructor 34 and an algorithm stored in storage device 38. To perform the automatic extraction of the ROI data the algorithm utilizes the projection data, or sinogram, for a desired z-location obtained using interpolation, as described above. Having obtained the sinogram for a z-position and for at least two gantry 12 rotations containing at least one cardiac cycle, a mean sinogram for one rotations is obtained by averaging the sinograms from each rotation of gantry 12. This average sinogram is then subtracted form the original sinogram of each rotation to obtain a motion sinogram. Regions of the object being scanned that are undergoing motion are identified by areas having a large magnitude in the motion sinogram. Therefore, a region of motion, or the ROI, is determined. All subsequent reconstruction processing is performed using the projection views from the ROI, and the final reconstructed images are centered on the ROI, for example the heart region.

Following the automatic extraction of the ROI projection data, spatial moments of the object in the projection space, i.e. a cross section of a person's chest, are calculated. Generally, the $n^{th}$ moment of distribution f(x) about a point $x_0$ is the integral of $(x-x_0)^n df(x)$, where df(x) is the incremental measurement of f(x). More specifically, Helgason-Ludwig consistency conditions state that spatial moments of projections can be obtained, for example, using:

$$M_k = \int s^k Rf(s, \theta) ds,$$

where $M_k$ is the $k^{th}$ order moment of a homogeneous polynomial of degree k in $\sin\theta$ and $\cos\theta$, and $Rf(s,\theta)$ is the Radon transformation of the object.

Once the spatial moments are calculated, the moments are normalized. Generally, normalization is defined as adjusting the representation of a quantity so that the representation lies within a prescribed range. More specifically, the normalized moments are determined by obtaining an average moment from multiple rotations of gantry 12 and dividing each individual spatial moment calculated by the average moment. The data from the normalized spatial moments is graphically plotted to illustrate peaks in the $k^{th}$ order moments $M_k$. In the exemplary embodiment, the normalized spatial moments are plotted to illustrate peaks in the first order moments $M_1$. The peaks in the normalized spatial moment data, i.e., the peaks in $M_1$, correspond to R-peaks in an EKG. Using the identified normalized peaks, the phases of the cardiac cycle are mapped to the temporal locations of the projections views. Therefore, all the projection views of the projection data are correlated, or tagged, with an associated cardiac phase using peaks of the normalized spatial moments.

Thus, in addition to each view being correlated, or tagged, with z-location data, each view is also tagged with cardiac phase information based on the peaks in the normalized moments, such as $M_1$. Using the projection data from the views tagged with phase and z-location data, a reconstruction technique obtains two-dimensional images of a beating heart at a desired cardiac phase and then reconstructs a three-dimensional image utilizing the two-dimensional image. Any known reconstruction technique can be used to reconstruct a three-dimensional image of a beating heart using the views tagged with phase and z-location data, for example, the filtered back projection technique described in, Principles of Computerized Tomographic Imaging, by A. C. Kak and M. Slaney, IEEE Press, New York N.Y., 1988.

While the invention has been described in terms of various specific embodiments, those skilled in the art will recognize that the invention can be practiced with modification within the spirit and scope of the claims.

What is claimed is:

1. A method for reconstructing an image of a beating heart in vivo, said method comprising:
   acquiring projection data for at least one z-location within a projection space;
   determining peaks in spatial moments for the projection space using the projection data; and
   reconstructing the image utilizing peaks in the spatial moments.

2. A method in accordance with claim 1 wherein acquiring a projection data comprises:
   correlating a plurality of views with z-location information, wherein each view includes projection data acquired at the respective z-location; and
   interpolating the projection data from each view to determine projection data at a desired z-location.

3. A method in accordance with claim 1 wherein determining peaks in the spatial moments comprises automatically extracting projection data for a region of interest (ROI) within each z-location.

4. A method in accordance with claim 3 wherein determining peaks in the spatial moments further comprises calculating spatial moments in the projection space using the ROI projection data.

5. A method in accordance with claim 4 wherein determining peaks in the spatial moments further comprises normalizing the spatial moments to determine the peaks.

6. A method in accordance with claim 1 wherein reconstructing the image comprises correlating a plurality of views with cardiac phase information based on the peaks in the spatial moments, wherein each view includes projection data at a z-location.

7. A method in accordance with claim 1 wherein reconstructing the image comprises utilizing a plurality of views correlated with z-location data and cardiac phase information to obtain a plurality of two-dimensional images at desired z-locations and cardiac phases, wherein each view includes projection data relevant to a respective z-location and cardiac phase.

8. A method in accordance with claim 7 wherein reconstructing the image further comprises combining the plurality of two-dimensional images to construct at least one three-dimensional image.

9. A system for reconstructing an image of a beating heart in vivo, said system comprising a computed tomography (CT) device including an x-ray source, an x-ray detector aligned with said x-ray source, a data acquisition system (DAS) for collecting data from said x-ray detector, and an image reconstructor for reconstructing an image from the collected data, said system configured to: acquire projection data for at least one z-location within a projection space; correlate a plurality of views with z-location information, wherein each view includes projection data acquired at the respective z-location;
   extract projection data for a region of interest (ROI) within each z-location;
   determine peaks in spatial moments for the projection space using the projection data; and
   reconstruct an image utilizing peaks in said spatial moments.

10. A system in accordance with claim 9 wherein to acquire a plurality of projection data, said system configured to interpolate the projection data from each view to determine projection data at a desired z-location.

11. A system in accordance with claim 9 wherein to determine peaks in said spatial moments, said system configured to automatically extract projection data for the ROI within each z-location.

12. A system in accordance with claim 11 wherein to determine peaks in said spatial moments, said system further configured to:
   determine spatial moments in the projection space using the ROI projection data; and
   normalize said spatial moments to determine the peaks.

13. A system in accordance with claim 9 wherein to reconstruct the image, said system configured to:
   determine cardiac phase information based on the peaks in said spatial moments; and
   correlate each view with the cardiac phase information.

14. A system in accordance with claim 9 wherein to reconstruct the image, said system configured to utilize a plurality of views correlated with z-location data and cardiac phase information to obtain a plurality of two dimensional images at desired z-locations and cardiac phases.

15. A system in accordance with claim 14 wherein to reconstruct the image, said system further configured to construct a three-dimensional image by combining the plurality of two-dimensional images.

16. A computer readable medium encoded with a program executable by a computer for processing projection data for at least one z-location within a projection space to construct images of a beating heart in vivo, said program configured to instruct the computer to:
   extract projection data for a region of interest (ROI) within each z-location; and
   determine peaks in spatial moments for the projection space using the projection data.

17. A computer readable medium in accordance with claim 16 wherein to extract projection data, said program further configured to instruct the computer to automatically extract projection data for the ROI within each z-location.

18. A computer readable medium in accordance with claim 16 wherein to determine peaks in said spatial moments, said program further configured to instruct the computer to calculate spatial moments in the projection space using the ROI projection data.

19. A computer readable medium in accordance with claim 18 wherein to determine peaks in said spatial moments, said program further configured to instruct the computer to normalize said spatial moments to determine the peaks.

20. A computer readable medium in accordance with claim 16 wherein said program further configured to instruct the computer to:
   determine cardiac phase information utilizing the determined peaks in said first order spatial moments; and
   correlate a plurality of views with the cardiac phase information.

21. A method for reconstructing an image of a beating heart in vivo, said method comprising:
   interpolating acquired projection data from a plurality of views to determine projection data at a plurality desired z-locations;
   automatically extracting projection data for a region of interest (ROI) within each desired z-location;
   determining peaks in first order spatial moments for a projection space using the extracted ROI projection data;
   determining cardiac phase information based on the peaks in the first order spatial moments; and
   reconstructing the image utilizing the cardiac phase information.

22. A method in accordance with claim 21 wherein determining peaks in first order spatial moments comprises:
   calculating spatial moments in the projection data using the extracted ROI projection data; and
   normalizing the spatial moments to determine the peaks.

23. A method in accordance with claim 21 wherein reconstructing comprises:
   correlating the plurality of views with the cardiac phase information;
   utilizing the plurality of views correlated with the cardiac phase information to obtain a plurality of two-dimensional images at a desired z-locations and cardiac phases; and
   combining the plurality of two-dimensional images to construct at least one three-dimensional image.

24. A system for reconstructing an image of a beating heart in vivo, said system comprising a computed tomography (CT) device including:
   a data acquisition system (DAS), configured to:
      acquire projection data for at least one z-location within a projection space; and
      interpolate the projection data to determine projection data for at least one view having at least one desired z-location;
   a computer electrically coupled to the DAS configured to:
      automatically extract projection data for a region of interest (ROI) within each desired z-location;
      determine peaks in first order spatial moments for the projection space using the projection data; and
      correlate each view with cardiac phase information; and an image reconstructor configured to reconstruct an image utilizing peaks in the first order spatial moments.

25. A system in accordance with claim 24 wherein to determine peaks in first order spatial moments, said computer further configured to:

determine spatial moments in the projection space using the extracted ROI projection data; and normalize said spatial moments to determine peaks.

26. A system in accordance with claim 24 wherein to correlate each view with cardiac phase information, said computer further configured to determine the cardiac phase information utilizing determined peaks in the first order spatial moments.

27. A system in accordance with claim 24 wherein to reconstruct a three-dimensional image, said reconstructor further configured to:

utilize a plurality of views correlated with cardiac phase information to obtain a plurality of two-dimensional images at desired z-locations and cardiac phases; and combine the two-dimensional images to construct at least one three-dimensional image.

28. A computer readable medium encoded with a program executable by a computer for processing projection data for at least one z-location within a projection space to construct images of a beating heart in vivo, said program g configured to instruct the computer to:

automatically extract projection data for a region of interest (ROI) within each z-location;

determine peaks in first order spatial moments for the projection space using the projection data;

determine cardiac phase information utilizing the peaks in said first order spatial moments; and correlate a plurality of views with the cardiac phase information.

29. A computer readable medium in accordance with claim 28 wherein to determine peaks in said first order spatial moments, said program further configured to instruct the computer to calculate spatial moments in the projection space using the ROI projection data.

30. A computer readable medium in accordance with claim 29 wherein to determine peaks in said first order spatial moments, said program further configured to instruct the computer to normalize said spatial moments to determine the peaks.

* * * * *